United States Patent [19]

Carlson et al.

[11] 4,250,891

[45] Feb. 17, 1981

[54] DEPTH-SENSE PERCEPTION AND TWO-POINT DISCRIMINATION AESTHESIOMETERS

[75] Inventors: Walter S. Carlson, Cincinnati, Ohio; Shlomo Samueloff, Jerusalem, Israel; Donald E. Wasserman, Cincinnati, Ohio

[73] Assignee: The United States of America as represented by the Department of Health, Education & Welfare, Washington, D.C.

[21] Appl. No.: 46,431

[22] Filed: Jun. 7, 1979

[51] Int. Cl.³ .............................................. A61B 5/16
[52] U.S. Cl. .................................................... 128/744
[58] Field of Search .............................. 128/739, 744; 35/DIG. 2

[56] References Cited

U.S. PATENT DOCUMENTS

| | | | |
|---|---|---|---|
| 1,174,275 | 3/1916 | Pitcher | 128/26 |
| 1,619,491 | 3/1927 | Smith | 297/159.1 |
| 2,315,160 | 3/1943 | Newstedt et al. | 128/744 |
| 2,508,146 | 5/1950 | D'Elia | 35/22 |
| 3,074,395 | 1/1963 | Kevorkian | 128/744 |
| 3,411,498 | 11/1968 | Reiter | 128/62 |
| 3,662,744 | 5/1972 | Low | 128/744 |
| 3,747,589 | 7/1973 | Harrison et al. | 128/744 |
| 3,933,148 | 1/1976 | Wyler et al. | 128/744 |

OTHER PUBLICATIONS

NASA Tech. Brief #66-10647, Dec. 1966, 1 page.
Carlson, W. S. et al., *Journ. of Occupational Med.*, Apr., 1979, vol. 21, No. 4, pp. 260-264.

*Primary Examiner*—Kyle L. Howell
*Attorney, Agent, or Firm*—Browdy and Neimark

[57] ABSTRACT

A finger tip sensitivity-testing instrument consisting of a tunnel-shaped track member used as a support for the hand and forearm of a patient, the track member having a longitudinal cavity slidably receiving a feeler bar which is formed on its top surface with surface profile structure varying progressively longitudinally in sensible magnitude. The patient's finger is received in a notch in the edge of the tunnel top wall so as to allow the finger to engage the surface profile bar as it is extended from the tunnel. Graduations are inscribed along the side margin of the feeler bar which represent specific increments of differential surface profile relative to the mouth of the tunnel. The feeler bar rests slidably on a spring-supported plastic thin plate, thus simulating a floating support surface for the feeler bar.

18 Claims, 13 Drawing Figures

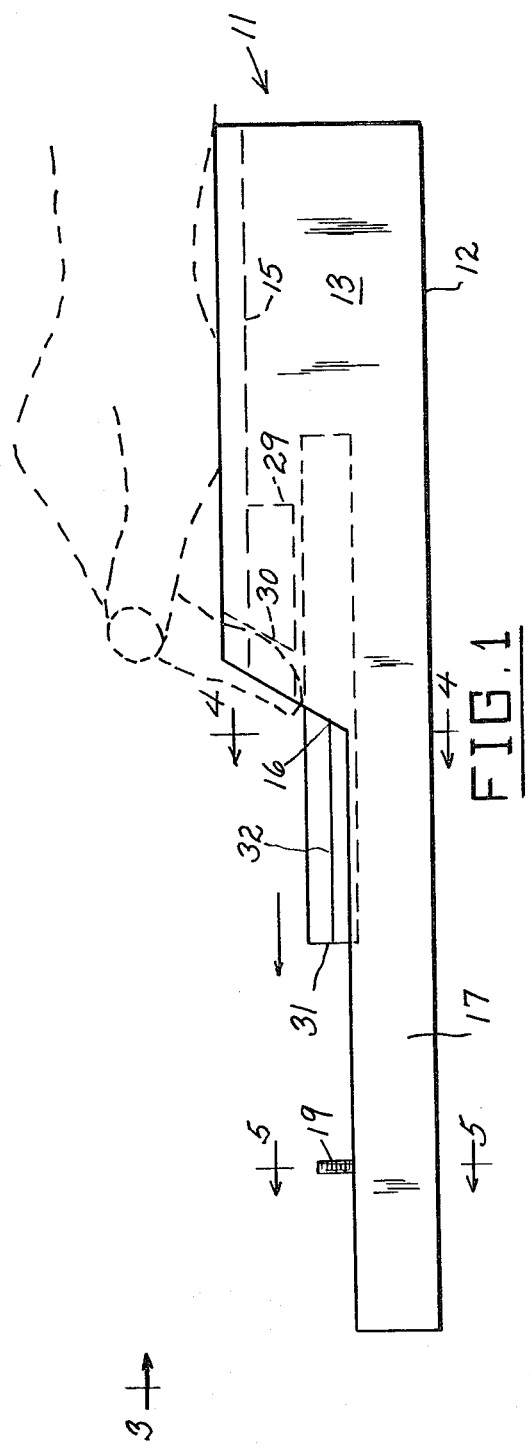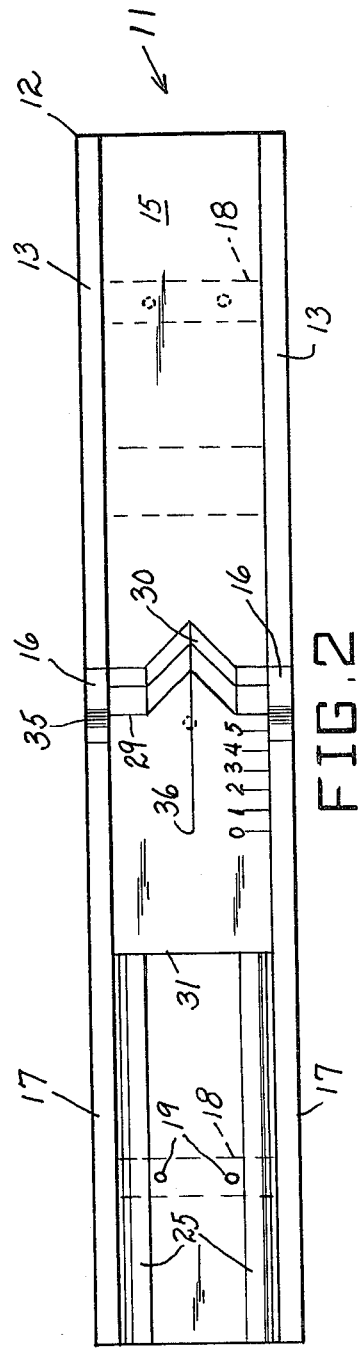

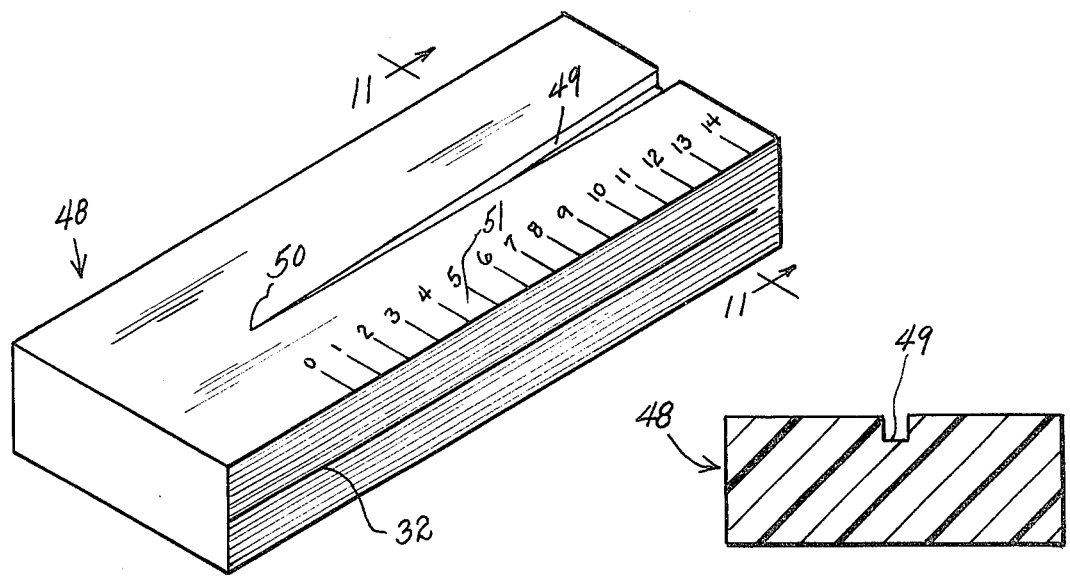
FIG.10
FIG.11
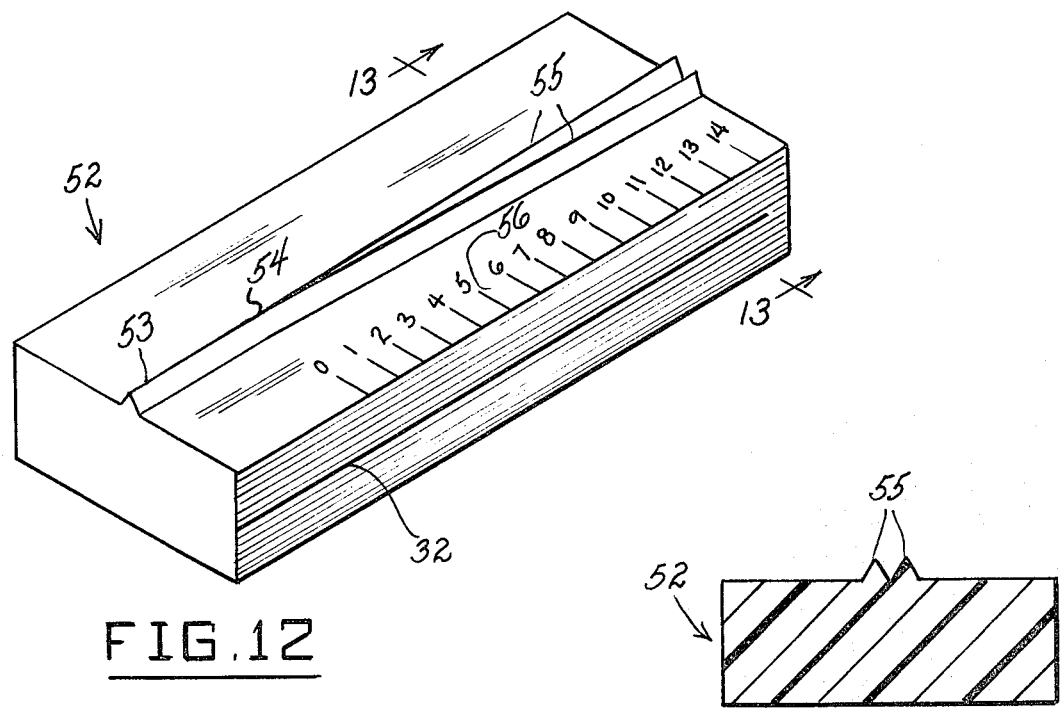
FIG.12
FIG.13

DEPTH-SENSE PERCEPTION AND TWO-POINT DISCRIMINATION AESTHESIOMETERS

FIELD OF THE INVENTION

This invention relates to instruments for measuring sensory perception, and more particularly to means for quantitatively measuring fingertip sensory perception in humans.

BACKGROUND OF THE INVENTION

Objective testing methods and means for the clinical diagnosis of Raynaud's Phenomenon of occupational origin (vibration-induced white finger disease) and for assessing patient disability arising from long-term usage of hand-held vibrating tools are at present inadequate. Peripheral blood flow measurements utilizing plethysmographic and ultrasonic techniques have been used (see Zweifler, "Detection of Occlusive Arterial Disease in the Hand and its Relevance to Occupational Hand Disease," Proceedings of the International Occupational Hand-Arm Vibration Conference, pp 12–17 DHEW (NIOSH) Publication No. 77-110, Cincinnati, Apr. 1977, and Laroche, "Traumatic Vasospastic Disease in Chain-Saw Operators," Can. Med. Assoc. J., 115:1217, 1976). To detect changes in the peripheral nervous system, the depth-sense and the two-point discrimination aesthesiometers were developed by Renfrew (see Renfrew, "Aesthesiometers," The Lancet, 1:1011, 1960, and Renfrew, "Fingertip Sensation. A Routine Neurological Test," The Lancet, 1:396, 1969). Both instruments have been used in a survey of pedestal grinders (see Pelmear, Taylor and Pearson, "Raynaud's Phenomenon in Pedestal Grinders," in The Vibration Syndrome, W. Taylor, London: Academic Press, Inc., 1974, pp 141–147), and the results show a loss in fingertip sensation. Mackworth (Mackworth, "Finger Numbness in Very Cold Winds," J. Appl. Physiol., 5:533–543, 1952–53) used a two-point discrimination instrument in assessing finger numbness when exposed to cold environments.

As above mentioned, previously used testing devices for assessing loss of fingertip sensory perception have been unsatisfactory and inadequate because they are relatively complicated, expensive and difficult to use. There is a substantial need for testing instruments with improved sensitivity, reliability and versatility, and which are simpler to use than the previously employed devices.

SUMMARY OF THE INVENTION

The present invention is intended to meet the above-mentioned need for a simplified yet quantitative means of assessing loss of fingertip sensory perception in humans. The devices of the present invention may be employed for testing a large number of workers using vibratory hand tools for possible loss in fingertip sensation. They can also be used to test for the possible sensory loss in workers exposed to toxic substances, such as pesticides, vinylchloride and carbon disulfide which might affect the peripheral nervous system. Consequently, these instruments will be useful in clinics, hospitals and departments for occupational medicine. The instruments of the present invention are thus useful for diagnostic and prognostic purposes in connection with initially testing such individuals and in monitoring their response to subsequent therapy.

The improvement and simplification of the instruments according to the present invention permits better sensitivity measurement, thus creating a better differentiation of abnormalities, provides consistency of measurement, and also provides a non-invasive means of detecting peripheral nerve damage. The instruments are preferably made of acrylic plastic, or other suitable material of low heat conductivity, so as to reduce the influence of temperature.

In general, a fingertip sensitivity testing instrument according to the present invention comprises a tunnel-shaped track member which is employed in a standardized manner as a support for the hand and forearm of a patient, the track member having a longitudinal guide cavity slidably receiving and surrounding a feeler bar, the bar being formed on its top surface with a longitudinally varying profile which changes progressively in sensible magnitude. A notch or similar guide structure is provided on the tunnel top wall transverse edge overlying the feeler bar for receiving and centering the patient's finger so as to allow the finger to engage the progressively changing surface profile of the feeler bar as it is gradually extended from the tunnel. Graduations are provided along one or both of the longitudinal margins of the feeler bar which represent specific increments of differential surface profile variations relative to the mouth of the tunnel. The feeler bar is resiliently supported in the tunnel by cushioned plate means which simulates a floating supporting surface for the feeler bar.

Accordingly, a main object of the invention is to provide a novel and improved fingertip sensitivity testing instrument which overcomes the deficiencies and disadvantages of previous devices used for testing and evaluating fingertip sensory perception in humans.

A further object of the invention is to provide an improved and simplified quantitative testing means for non-invasively assessing loss of fingertip sensory perception in persons using vibratory hand tools or exposed to toxic substances which might affect the peripheral nervous system.

A still further object of the invention is to provide an improved instrument for testing fingertip sensory perception, either with respect to depth-sensing perception or with respect to lateral spread or 2-point discrimination.

A still further object of the invention is to provide an improved fingertip sensory perception testing instrument which is easy to use, which provides uniformly reproducible finger and hand-supporting conditions for testing, and which is not affected by changes in temperature.

A still further object of the invention is to provide an improved finger sensory perception-testing instrument which is inexpensive to fabricate, which is durable in construction, which is versatile in use, which provides a patient with a comfortable arm position during testing, and which minimizes differences in pressure and positioning of the fingers under examination.

A still further object of the invention is to provide an instrument which facilitates the testing of a patient's fingertip sensory perception by allowing the patient's hand and forearm to rest on a stable and comfortable surface, with the finger to be tested positioned in a V-shaped notch or groove provided on the support, which centers the finger and prevents lateral movement thereof during testing.

A still further object of the invention is to provide an improved instrument for testing a patient's fingertip sensory perception by providing a stable stationary support for the patient's hand and forearm while the finger being tested engages a movable progressively profiled feeler bar which is resiliently supported and wherein the reaction pressure of the feeler bar on the finger can be adjusted by matching the feeler bar's elevation with respective marked zones on side edge portions of the stationary support at opposite sides of the feeler bar.

BRIEF DESCRIPTION OF THE DRAWINGS

Further objects and advantages of the invention will become apparent from the following description and claims, and from the accompanying drawings, wherein:

FIG. 1 is a side elevational view of an improved fingertip sensitivity-testing instrument according to the present invention.

FIG. 2 is a top plan view of the instrument of FIG. 1.

FIG. 10 is an enlarged perspective view of a feeler bar according to the present invention, used in the instrument of FIGS. 1 to 5 for lateral spread or 2-point discrimination finger sensitivity measurements.

FIG. 11 is a transverse vertical cross-sectional view taken substantially on line 11—11 of FIG. 10.

FIG. 12 is an enlarged perspective view of another feeler bar according to the present invention, used for lateral spread or 2-point discrimination finger sensitivity measurements.

FIG. 13 is a transverse vertical cross-sectional view taken substantially on line 13—13 of FIG. 12.

DETAILED DESCRIPTION OF PREFERRED EMBODIMENTS

Figure 3:
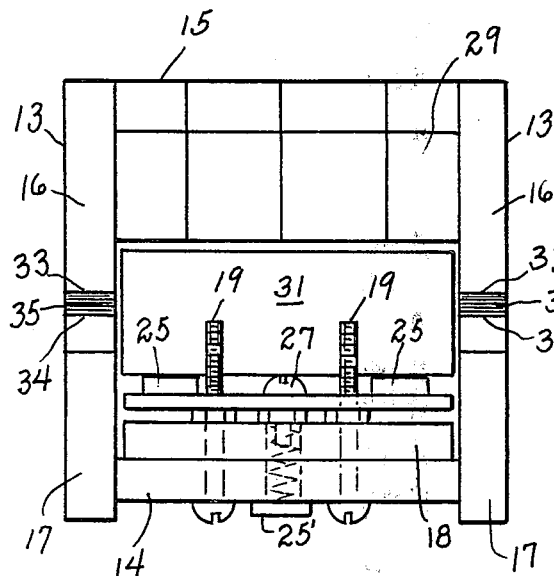
FIG. 3 is an enlarged end elevational view taken substantially on line 3—3 of FIG. 1.

Referring to the drawings, 11 generally designates a typical fingertip sensitivity-testing instrument constructed in accordance with the present invention. The instrument 11 comprises a generally tunnel-shaped rectangular housing 12 with parallel vertical longitudinal side walls 13, 13, a horizontal bottom wall 14, and a horizontal top wall 15. The side walls 13, 13 are cut away approximately at the midportion of the housing to define downwardly and leftwardly inclined parallel straight shoulder edges 16, 16, as viewed in FIG. 1, and reduced-height side wall portions 17, 17. The edges 16, 16 may be in a common transverse plane inclined approximately 30° from the vertical.

Figure 4:
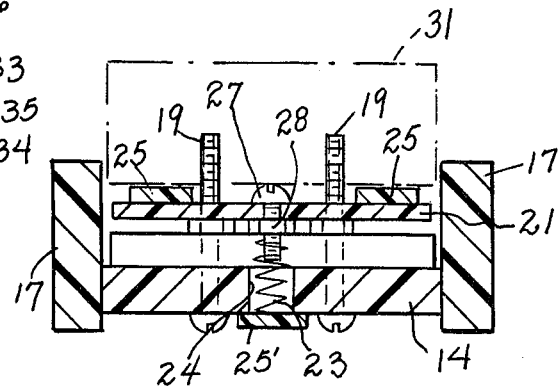
FIG. 4 is an enlarged transverse vertical cross-sectional view taken substantially on line 4—4 of FIG. 1.
Figure 5:
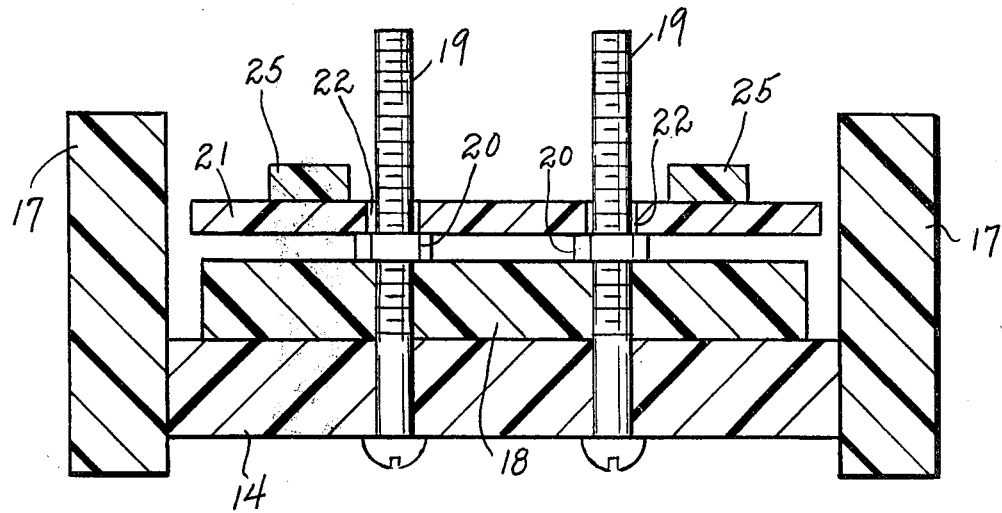
FIG. 5 is a further enlarged transverse vertical cross-sectional view taken substantially on line 5—5 of FIG. 1.

Respective transversely extending cross bars 18, 18 are rigidly secured on bottom wall 14 adjacent its opposite ends by means of respective pairs of upstanding bolts 19, 19 and clamping nuts 20, 20, as shown in FIG. 5. A longitudinally extending thin elongated plate-like member 21 is disposed over the cross bars 18, 18, the member 21 being formed with respective pairs of holes 22, 22 adjacent its opposite ends loosely receiving the respective pairs of bolts 19, 19 and being engageable on the associated clamping nuts 20, 20 to limit downward movement of the plate-like member 21. Said member 21 is resiliently biased upwardly at its central portion, namely, adjacent the shoulder edges 16,16, by a coiled spring 23 (see FIG. 4) seated in a central hole 24 provided in bottom wall member 14 and bearing on a bottom cover plate 25 rigidly cemented to bottom wall 14 beneath hole 24. The top portion of spring 23 receives a positioning screw 27 extending centrally through the plate-like member 21 and clamped thereto by a nut 28. Spring 23 bears upwardly on nut 28 and resiliently urges plate-like member 21 upwardly at its center portion, namely, adjacent the plane of the inclined shoulder edges 16, 16, and provides a floating supporting action for said plate-like member 21.

Rigidly cemented on member 21 are two rail members 25, 25 located inwardly adjacent to and substantially coextensive with the opposite longitudinal side edges of member 21. In a typical embodiment, the plate-like member 21 was $\frac{1}{8}$ inch thick, $2\frac{1}{8}$ inches wide and 27 inches long. The cross bars 18 were $\frac{1}{4}$ inch thick, 5/16 inch wide and 2 inches long. Bolts 19 were $1\frac{1}{4}$ inch long, 6-32 bolts, and holes 22 were 3/16 inch in diameter. Plate-like member 21 was a plastic sheet formed centrally with a $\frac{1}{8}$ inch hole to receive the guide screw 27, which was a $\frac{1}{2}$ inch long, 6-32 screw, fastened by the nut 28 with the bolt head uppermost, as shown in FIG. 4. The depending stem of screw 27 fits inside the spring 23 to maintain the vertical positioning of the spring. In said typical embodiment, the plastic plate-like sheet member 21 spanned a distance of approximately 23 inches between the transverse support bars 18, 18. The spring 23, being located centrally, provides an upward force on the plastic sheet member 21, creating an effect simulating a floating surface.

A thickening block 29 is cemented beneath top wall 15 and is formed so as to be flush with the leftwardly-facing tunnel top wall edge, as viewed in FIG. 1. A finger-centering notch or groove 30, which is substantially V-shaped, is centrally formed in the flush leftwardly facing edges of top wall 15 and block 29. The notch 30 forms a V-shaped channel which is inclined downwardly and leftwardly, parallel to the common plane of the inclined side shoulder edges 16, 16.

A feeler bar, or aesthesiometer, 31 is slidably supported on the pair of parallel rail members 25, 25 and is slidably receivable in the tunnel-shaped housing, as shown in FIGS. 1 to 4, being guided thereby for longitudinal movement on said rail members.

Finger pressure calibration lines 32 are etched, or otherwise suitably inscribed, on the opposite longitudinal edges of the feeler bars used with the instrument, including the feeler bar 31 and others to be presently described in detail. In calibrating the instrument for finger pressure, with a feeler bar supported on the rails 25, 25 with no finger pressure thereon, a first pair of horizontal lines 33, 33 are drawn on edges 16, 16 at the level of the calibration lines 32, 32. A 100 gram weight is then placed on the feeler bar and a second pair of horizontal lines 34, 34 are drawn on edges 16, 16 at the new level of calibration lines 32, 32. The area between the marks 33,34 on the respective edges 16, 16 is then painted or otherwise suitably shaded, as shown at 35, 35. These areas 35, 35 thus become the correct-pressure calibration indicators with respect to finger pressure applied on the feeler bar by a patient.

Figure 6:
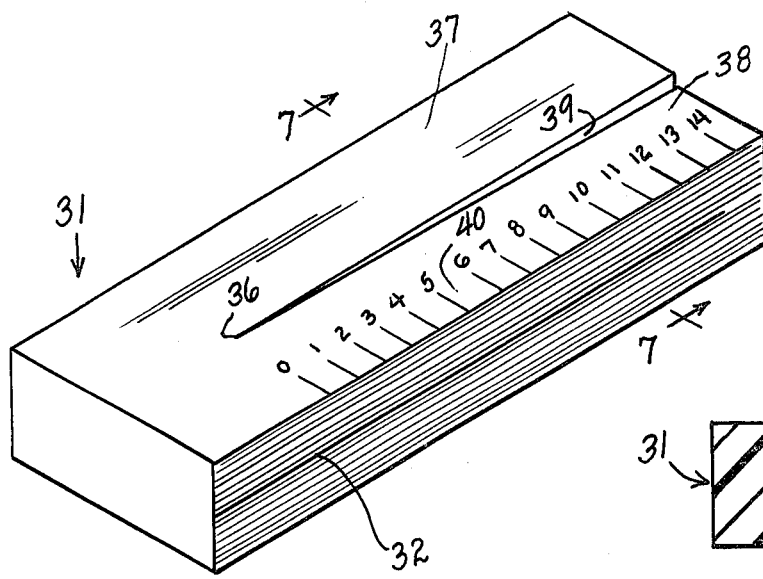
FIG. 6 is an enlarged perspective view of a feeler bar according to the present invention used in the instrument of FIGS. 1 to 5 for depth perception fingertip sensitivity measurements.
Figure 7:
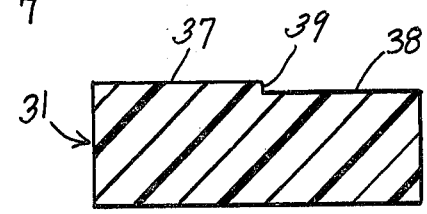
FIG. 7 is a transverse vertical cross-sectional view taken substantially on line 7—7 of FIG. 6.

The feeler bar, or aesthesiometer, 31 shown in detail in FIGS. 6 and 7, is for use in testing depth-sense perception. It has a split top surface along its longitudinal center line, commencing at a zero point 36 located 5 cm from the left end of the bar, as viewed in FIG. 6. Half of the split surface, shown at 37, remains level, and the other half, shown at 38, slopes downwardly toward the right end of the bar at a rate of 1 mm per 10 cm of horizontal distance, defining a vertical shoulder 39 which progressively increases in depth rightwardly. The total horizontal sensory length is 15 cm, making a maximum differential between surfaces 37 and 38 of 1.5 mm. This provides a single edge for the perception of depth-sense. A scale 40 of progressive graduations is inscribed at one side margin of the bar, for each centimeter from the zero point 36, which represent increments of 0.1 mm of depth between the split surfaces 37, 38.

Figure 8:
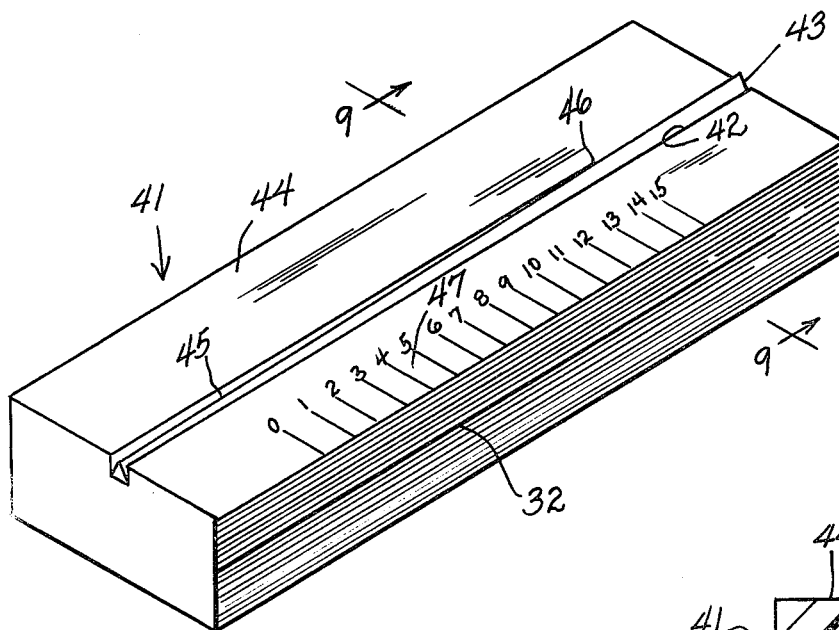
FIG. 8 is an enlarged perspective view of another feeler bar according to the present invention, used for depth perception finger sensitivity measurements.
Figure 9:
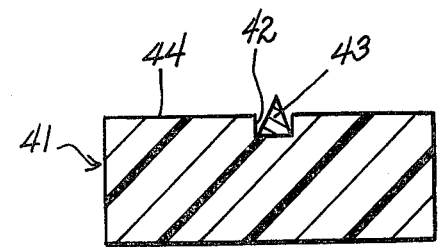
FIG. 9 is a transverse vertical cross-sectional view taken substantially on line 9—9 of FIG. 8.

Another feeler bar, or aesthesiometer, for use in testing depth-sense perception is shown in FIGS. 8 and 9 and is designated at 41. The feeler bar 41 has a longitudinal channel 42 along the longitudinal center line, said channel being 6 mm wide and 5 mm deep. Secured in channel 42 is an inverted V-shaped solid rod 43. The top edge of ridge of the rod 43 remains flush with the top surface 44 of the feeler bar for the first 5 cm from the left end of the bar, as viewed in FIG. 8, to a point 45. It then rises progressively at the same rate as in FIG. 6, namely, 1 mm per 10 cm of length, along a longitudinal distance of 15 cm to a point 46. For the remaining 5 cm the height remains constant. A scale 47 of 1 cm-interval graduations is inscribed along one longitudinal side margin of the feeler bar.

Another feeler bar, or aesthesiometer, for use in testing spread perception, or 2-point discrimination, is shown at 48 in FIGS. 10 and 11. The feeler bar 48 has a 5 mm-deep wedge shaped channel 49 formed in its top surface along its longitudinal center line, beginning 5 cm from its left end, as viewed in FIG. 10, at a point 50. Beginning from the point 50 the wedge-shaped channel 49 progressively spreads at a rate of 0.4 mm per cm for the remaining 15 cm of longitudinal length. A scale 51 of graduations in centimeters is engraved or suitably inscribed along one longitudinal side margin of the feeler bar, starting from the location of the zero point 50.

Another feeler bar, or aesthesiometer, for use in testing spread perception, or 2-point discrimination, is shown at 52 in FIGS. 12 and 13. An inverted V-shaped rib, 5 mm in height, extends from the left end of the feeler bar top surface along its longitudinal center line for a distance of 5 cm to a point 54, where said rib branches into two rightwardly divergent inverted V-shaped ribs 55, 55, also 5 mm in height, progressively diverging for the remaining 15 cm of length of the feeler bar. A scale 56, graduated in centimeters is inscribed along a side margin of the feeler bar, beginning at the location of the zero point 54.

As mentioned above, the various parts of the instrument are preferably made of material of low heat conductivity, such as acrylic plastic, or the like, to minimize temperature interference effects.

There are various ways of testing fingertip sensation with the above-described apparatus. The patient may actively move his finger over a feeler block, or the examiner may grasp the patient's finger and passively move it on a block. Alternatively, the patient's finger may be held stationary either by himself or by the examiner while the block is moved.

It is preferable to use the total instrument 11 rather than the blocks individually, since this provides the patient with a comfortable arm position and reduces differences in pressure on and positioning of the examined finger. Thus, as shown in dotted view in FIG. 1, the patient's hand and forearm rest on top of the housing 12 with the finger to be tested positioned in the 60°-inclined V-shaped groove 30. The groove 30 centers the finger and prevents lateral movement thereof. With the hand and forearm resting on the top housing 12 and the finger to be tested positioned in groove 30, the finger pressure is adjusted by matching the inscribed lines 32 with the shaded zones 35, as above described. The finger is thus passively held in a stationary and constant position and pressure while the feeler bar is moved under the patient's finger, away from the patient. To prevent patient bias, the actual starting position of testing occurs variably before the zero point of the longitudinal distance scale at the side margin of the feeler bar. The patient is instructed to look away from the instrument during the measurements. Several measurements are obtained for each finger of each hand, using the different types of feeler bars, presented randomly.

When the patient states that he senses the feeling of depth or spread of the feeler bars, readings are taken from the graduated length scales at the side margins of the feeler bars and are suitably recorded.

The results of the tests are used for assessing the degree of possible sensory loss or its impairment of the fingers.

While certain specific embodiments of devices for measuring fingertip sensory perception have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A fingertip sensitivity measuring device comprising a housing having a recess therein, a feeler bar horizontally slidable within said housing and being extensible from the mouth of the recess, said feeler bar having a top surface with a profile which changes progressively along its length starting at a point spaced from the end thereof, and means on said housing to support the hand of a patient with a finger extended over the mouth of the recess to touch the feeler bar, said housing and feeler bar being provided with cooperating scale and index means to measure the extension of the feeler bar relative to the mouth of the recess.

2. The fingertip sensitivity measuring device of claim 1, and wherein said mouth portion includes a top edge formed with a guide notch to receive the patient's finger.

3. The fingertip sensitivity measuring device of claim 1, and wherein the profile of the feeler bar has a configuration which changes progressively longitudinally in vertical height.

4. The fingertip sensitivity measuring device of claim 1, and wherein the profile of the feeler bar has a configuration which changes progressively longitudinally in horizontal width.

5. The fingertip sensitivity measuring device of claim 1, and wherein said cooperating scale and index means includes a length scale on a longitudinal margin of the feeler bar arranged substantially coextensively with the longitudinally progressively changing profile of the feeler bar top surface.

6. The fingertip sensitivity measuring device of claim 1, and wherein the top surface of the feeler bar has a non-changing longitudinal horizontal portion leading to said progressively changing profile.

7. A fingertip sensitivity measuring device comprising an elongated tunnel-shaped housing having a mouth portion, a feeler bar slidably engaged in said housing and being extensible longitudinally from said mouth portion, said feeler bar having a top surface with a profile which changes progressively along its length, and means on said housing to support the hand of a patient with a finger extended over said mouth portion to touch the feeler bar, said housing and feeler bar being provided with cooperating scale and index means to measure the extension of the feeler bar relative to said mouth portion, and wherein said housing includes resiliently-cushioned longitudinally extending bottom support means for said feeler bar.

8. The fingertip sensitivity measuring device of claim 7, and wherein said bottom support means includes a pair of spaced parallel longitudinal rail members for supportingly engaging the underside of said feeler bar.

9. The fingertip sensitivity measuring device of claim 7, and wherein said bottom support means comprises a longitudinally extending plate member underlying the feeler bar, and biasing spring means between the plate member and the bottom of said tunnel-shaped housing.

10. The fingertip sensitivity measuring device of claim 7, and wherein said bottom support means comprises a longitudinal plate member underlying the feeler bar, and biasing spring means between the plate member and the bottom of the tunnel-shaped housing, said biasing spring means being located substantially beneath the mouth portion of the housing.

11. The fingertip sensitivity measuring device of claim 10, and cooperating vertically extending guide pin and hole means on the bottom of the housing and on said longitudinal plate member.

12. The fingertip sensitivity measuring device of claim 10, and wherein said mouth portion has a centering notch in its top edge adapted to receive the patient's finger.

13. The fingertip sensitivity measuring device of claim 10, and cooperating marker means on the feeler bar and the mouth portion of the tunnel-shaped housing for indicating the degree of touching pressure exerted on the feeler bar by the patient's finger.

14. The fingertip sensitivity measuring device of claim 13, and wherein said marker means comprises a longitudinal line inscribed on a side edge of the feeler bar and a pressure-indicating marked zone on a side margin of said mouth portion adjacent said longitudinal line.

15. A fingertip sensitivity measuring device comprising an elongated tunnel-shaped housing having a mouth portion, a feeler bar slidably engaged in said housing and being extensible longitudinally from said mouth portion, said feeler bar having a top surface with a profile which changes progressively along its length, and means on said housing to support the hand of a patient with a finger extended over said mouth portion to touch the feeler bar, said housing and feeler bar being provided with cooperating scale and index means to measure the extension of the feeler bar relative to said mouth portion, and wherein the profile of the feeler bar comprises a configuration which is longitudinally split, forming on one side a constantly horizontal flat surface and on the other side a descending inclined surface to define a longitudinal shoulder edge of longitudinally changing height.

16. A fingertip sensitivity measuring device comprising an elongated tunnel-shaped housing having a mouth portion, a feeler bar slidably engaged in said housing and being extensible longitudinally from said mouth portion, said feeler bar having a top surface with a profile which changes progressively along its length, and means on said housing to support the hand of a patient with a finger extended over said mouth portion to touch the feeler bar, said housing and feeler bar being provided with cooperating scale and index means to measure the extension of the feeler bar relative to said mouth portion, and wherein said profile comprises means defining a longitudinally extending wedge-shaped recess defining horizontal longitudinally diverging edges at the top surface of the feeler bar.

17. In a fingertip sensitivity testing instrument, a feeler bar comprising a substantially rectangular block with a top surface which is longitudinally split, forming on one side a constantly horizontal flat surface and on the other side a descending inclined surface to define a longitudinal shoulder edge of longitudinally changing height, and wherein the top surface of the bar has a non-changing longitudinal horizontal portion leading to said shoulder edge and a longitudinal length scale substantially coextensive with said shoulder edge.

18. In a fingertip sensitivity testing instrument, a feeler bar comprising a substantially rectangular block with a top surface having a longitudinally extending wedge-shaped recess defining horizontal longitudinally diverging edges, and wherein said top surface has a longitudinal flat horizontal surface portion leading to the apex end of said wedge-shaped recess and a longitudinal length scale substantially coextensive with said recess.

* * * * *